(12) United States Patent
Holmqvist

(10) Patent No.: US 9,033,936 B2
(45) Date of Patent: May 19, 2015

(54) MEDICAMENT DELIVERY DEVICE

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 203 days.

(21) Appl. No.: 13/508,359

(22) PCT Filed: Oct. 29, 2010

(86) PCT No.: PCT/SE2010/051182
§ 371 (c)(1),
(2), (4) Date: May 5, 2012

(87) PCT Pub. No.: WO2011/056127
PCT Pub. Date: May 12, 2011

(65) Prior Publication Data
US 2012/0220953 A1 Aug. 30, 2012

(30) Foreign Application Priority Data
Nov. 6, 2009 (SE) ....................... 0950834

(51) Int. Cl.
*A61M 5/315* (2006.01)
*A61M 5/24* (2006.01)

(52) U.S. Cl.
CPC ............. *A61M 5/31551* (2013.01); *A61M 5/24* (2013.01); *A61M 5/31555* (2013.01); *A61M 5/31575* (2013.01); *A61M 5/31578* (2013.01)

(58) Field of Classification Search
CPC ..................... A61M 5/31528; A61M 5/31533; A61M 5/31548; A61M 5/3155; A61M 5/31553
USPC .......... 604/187, 207, 208, 211, 227, 228, 233
See application file for complete search history.

(56) References Cited

U.S. PATENT DOCUMENTS

| 4,498,904 A | * | 2/1985 | Turner et al. ................... 604/211 |
| 4,865,591 A | * | 9/1989 | Sams ............................. 604/186 |
| 2012/0283657 A1 | * | 11/2012 | Kouyoumjian et al. ....... 604/211 |

FOREIGN PATENT DOCUMENTS

| WO | 02/76536 A1 | 10/2001 |
| WO | 2004/041334 A2 | 5/2004 |
| WO | 2007/132019 A1 | 11/2007 |

OTHER PUBLICATIONS

Swedish Patent Office, Int'l Search Report in PCT/SE2010/051182, Feb. 15, 2011.
Swedish Patent Office, Written Opinion in PCT/SE2010/051182, Feb. 15, 2011.

* cited by examiner

*Primary Examiner* — Theodore Stigell
*Assistant Examiner* — Benjamin Koo
(74) *Attorney, Agent, or Firm* — Piedmont Intellectual Property

(57) ABSTRACT

Medicament delivery device comprising relatively movable housing parts, a medicament container, a proximal plunger rod part and distal plunger rod part in threaded engagement with each other, wherein said proximal plunger rod part is movably arranged in relation to said housing part sand in contact with a stopper of said medicament container, a lever pivotally attached to said housing parts and to the distal plunger rod part. The housing parts are ergonomically shaped having a grip-size for achieving a full hand grip and wherein said distal housing part and said proximal housing part are operably interconnected to each other through said lever such that a relative movement of said housing parts is capable of operating the lever for setting and injecting a dose.

6 Claims, 4 Drawing Sheets

MEDICAMENT DELIVERY DEVICE

TECHNICAL AREA

The present invention relates to a medicament delivery device and in particular an ergonomic manually operated multi-dose medicament delivery device provided with reduced power demands.

BACKGROUND OF INVENTION

There are a number of medicament delivery devices that are intended for self-administration. Some of these devices are provided with automatic functions such as auto-penetration, auto-injection, auto-withdrawal, just to mention some. However, even if these functions facilitate the administration of medicament, the devices become rather complex to manufacture and there is an increased risk for mal-functioning of a function.

In these aspects it would be desirable in many instances to have manually operated devices that are intuitive and easy to operate and inexpensive. However, for persons with reduced power of the hands and/or reduced dexterity of the hands, manual operation may be difficult because there is required a rather large force for performing a medicament delivery and in particular to overcome the break loose force of a stopper arranged inside a medicament container.

In view of this some devices have been developed for facilitating the handing of a syringe such that less force is required. Documents U.S. Pat. No. 5,336,201 and WO 2002/094343 both display delivery devices having a gripping handle and a lever pivotally attached to the handle, where the lever is acting on either a separate piston that is capable of drawing medicament from a container to a patient (U.S. Pat. No. 5,336,201) or acting on a plunger of the syringe (WO 2002/094343). The drawbacks with the design of the described devices is that they become rather bulky, looking like hand guns, which is not an advantage when a user has to carry the device with him daily nor to use it publically.

WO 2007/132019 relates to a pen-injector that comprises a lever gearing designed to provide increase power during manual injection. The device also allows dose setting. A drawback is the thin shape with a push button at the distal end, which make it difficult for the manually impaired to operate.

There is thus room for improvement regarding manually operated medicament delivery device which are provided with force assistance.

BRIEF DESCRIPTION OF INVENTION

The aim of the present invention is remedy the drawbacks of the state of the art medicament delivery devices.

This aim is obtained by a medicament delivery device with the features of the independent patent claim.

Preferable embodiments of the invention form the subject of the dependent claims.

According to main aspect of the invention it is characterized by a medicament delivery device comprising a proximal housing part; a distal housing part; a medicament container arranged inside said proximal housing part; a plunger rod comprising a proximal plunger rod part and a distal plunger rod part in threaded engagement with each other, wherein said proximal plunger rod part is movably arranged in relation to said proximal housing part and in contact with a stopper of said medicament container, and wherein said housing parts are ergonomically shaped and have a grip size for achieving a full hand grip and wherein said distal housing part and said proximal housing part are operably interconnected to each other through said lever such that a relative movement of said housing parts is capable of operating the lever for setting and injecting a dose.

According to another aspect of the invention said proximal housing part comprises first locking members acting on the threads of said proximal plunger rod part such that said first locking members only allow proximal movement of said proximal plunger rod part.

According to yet another aspect of the invention said proximal housing part comprises second locking members acting on corresponding second locking members of said proximal plunger rod part such that said second locking members block rotational movement of said proximal plunger rod part.

According to a further aspect of the invention the distal plunger rod part comprises engagement means arranged to interact with corresponding engagement means of the distal housing part for rotationally locking said parts in relation to each other, such that a rotation of said distal housing part in relation to the proximal housing part, causes the distal plunger rod to be moved a certain distance in a distal direction in relation to the proximal housing part and the proximal plunger rod, and the lever to pivot, whereby said certain distance corresponds to a dose quantity to be delivered.

According to yet a further aspect of the invention said dose quantity is indicated by indicia on a side surface of the proximal housing part.

According to yet another aspect of the invention relative longitudinal movement of the housing parts towards each other causes the distal housing part to act on the lever such as to proximally displace the plunger rod parts in relation to the proximal housing part to deliver said dose quantity.

An advantage with the present invention is the use of a lever acting on the plunger rod for expelling a dose of medicament. This greatly reduces the force required to overcome the force holding the stopper within the medicament container such that a dose may be delivered.

Another advantage is that since said housing parts are ergonomically shaped and have a grip size for achieving a full hand grip and since said distal housing part and said proximal housing part are operably interconnected to each other through said lever, a user having dexterity problems can set and inject a dose in an easy way. The ergonomic shape of the proximal and the distal housing parts provides a good use of the whole hand when a dose is to be set and delivered instead of just relying on the fingers as is the case with a normal syringe.

The design of the device also provides the possibility of setting any required dose in a simple, intuitive and reliable way by turning the distal housing part in relation to the proximal housing part. The use of a plunger rod in two parts that are threaded into each other also provides the possibility of setting a required dose as well as shortening the length of the device.

A further advantage of a multi-dose delivery device according to the invention is the use of a locking device for locking movement of the proximal plunger in the distal direction, such that after delivery of a dose the stopper is prevented from distal movement in the container in order to improve dose accuracy.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
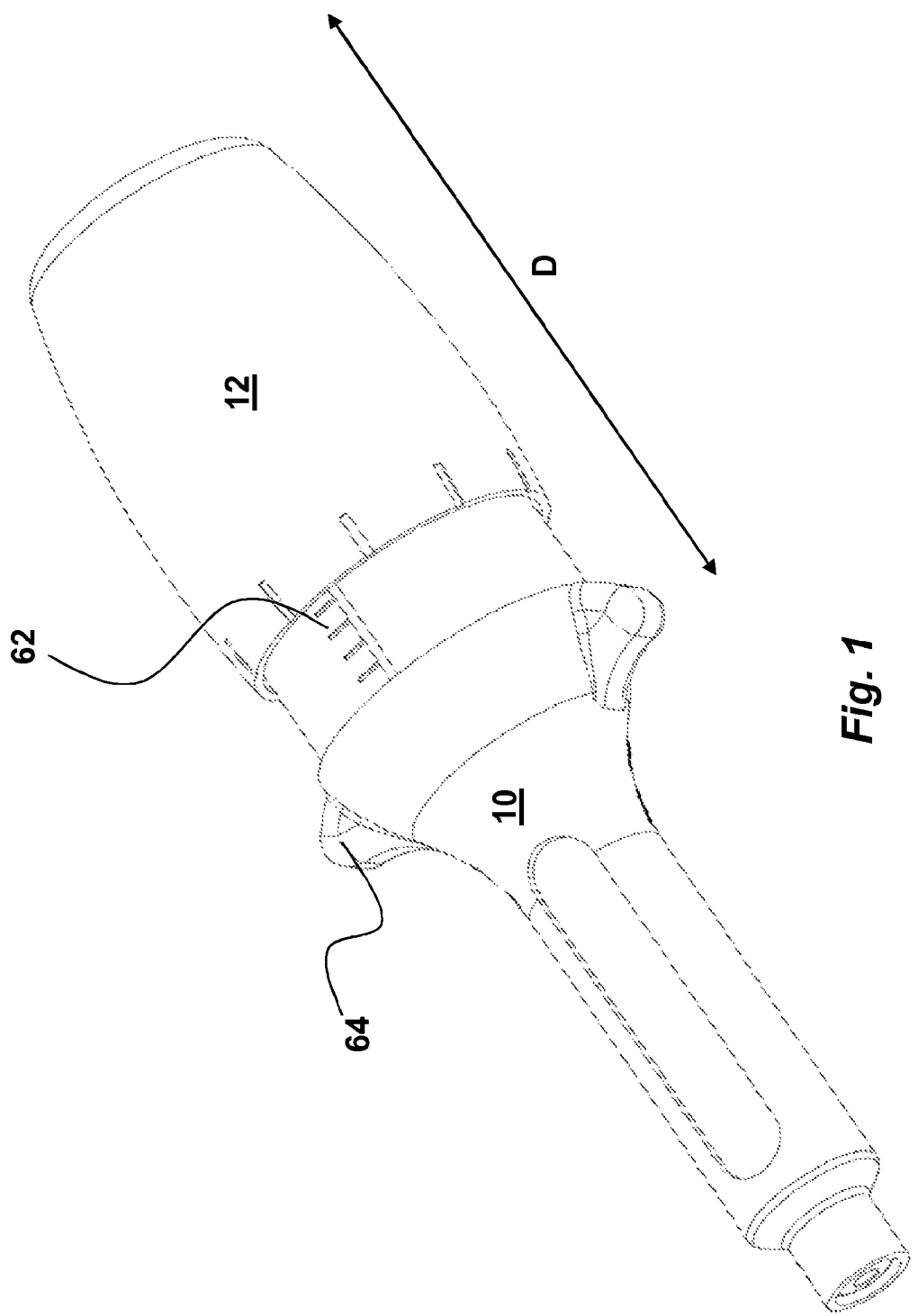
FIG. 1 is a perspective view of a medicament delivery device according to the present invention.

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

The medicament delivery device according to the present invention comprises a proximal housing part 10 and a distal housing part 12 movably connected to said proximal housing part. Inside a longitudinally extending passage 13 of the proximal housing part 10 a medicament container 14 is positioned with its neck portion 16 inside a proximal neck portion 18 of the proximal housing part 10, to which a medicament delivery member (not shown) may be attached, such as an injection needle, a mouthpiece, a nozzle and the like, FIG. 4.

In the present application, the wording grip size is defined as the distance D between the palm of the hand and the rest of the fingers, except the thumb, of a user's hand, when an object is gripped. See FIG. 1. Consequently, the grip size of an object is the distance between two opposite surfaces of a grip area.

The housing parts are ergonomically shaped for achieving a full hand grip. In the exemplary embodiment shown in FIG. 1 the distal end of the distal housing part 12 is adapted to comfortably rest in a user's palm. The rest of the fingers, except the thumb, may be placed around the grip members 64, such that the clenching of the hand pushes the housing parts together to cause an injection of a set dose of medicament. Since the grip size of the device varies with the set dose the largest grip size, i.e. corresponding to the largest available dose, should still allow a comfortable grip even for users having small hands. For setting a dose the housing parts are adapted to allow full hand grips on the device to turn the housing parts in relation to each other.

Further a plunger rod is arranged inside the housing parts 10, 12. The plunger rod comprises a proximal plunger rod part 22 and a distal plunger rod part 24 in threaded engagement with each other, wherein said proximal plunger rod part is movably arranged in relation to said proximal housing part and in contact with a stopper 20 of said medicament container, and wherein said distal plunger rod part is connected to said distal housing part, FIG. 2. The distal plunger rod part 24 is further arranged with engagement means 26, such as two longitudinally extending ledges on opposite side of the distal plunger rod part 24, arranged to interact with corresponding engagement means 28 such as longitudinally extending grooves on the distal housing part for rotationally locking said parts in relation to each other, FIG. 4. These ledges fit into the longitudinally extending grooves 28 arranged in a tubular guide part 30 attached to the inner surface of a distal end wall 32 of the distal housing part 12, FIG. 3.

Figure 3:
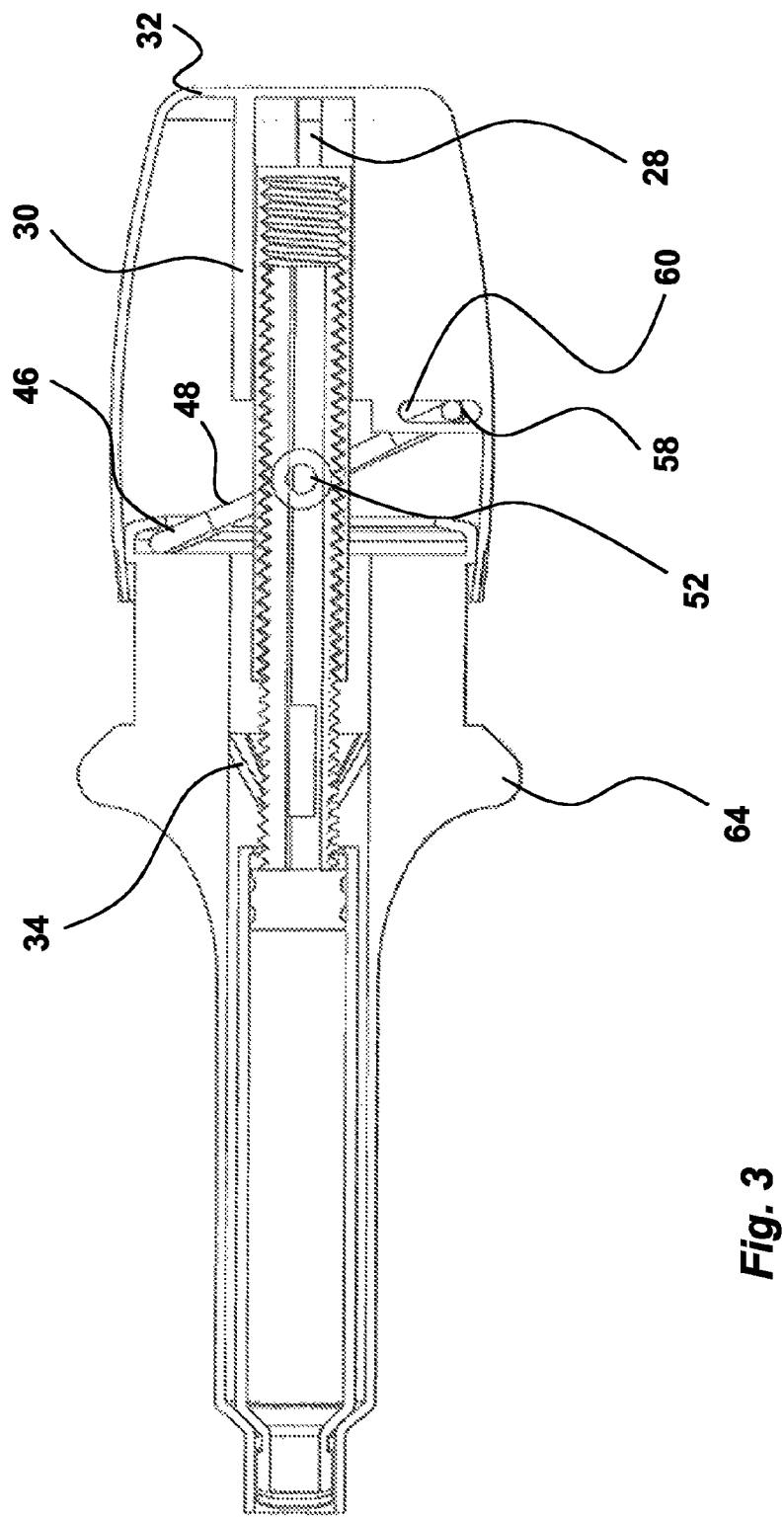
FIG. 3 is a cross-sectional side view of the device of FIG. 1 taken 90° in relation to FIG. 2.

Further the passage 13 of the proximal housing part 10 is arranged with first locking members 34 such as a number of inwardly, proximally inclined arms that are radially flexible but rigid in a distal direction and arranged to be in contact with the threads of the proximal plunger rod part 22 such that said first locking members 34 only allow proximal movement of said proximal plunger rod part, FIG. 3. During injection of medicament, the stopper is somewhat compressed by the applied pressure. Therefore dose accuracy can be improved by using such an arrangement to block distal movement of the proximal plunger as the stopper seeks to expand after injection.

Figure 4:
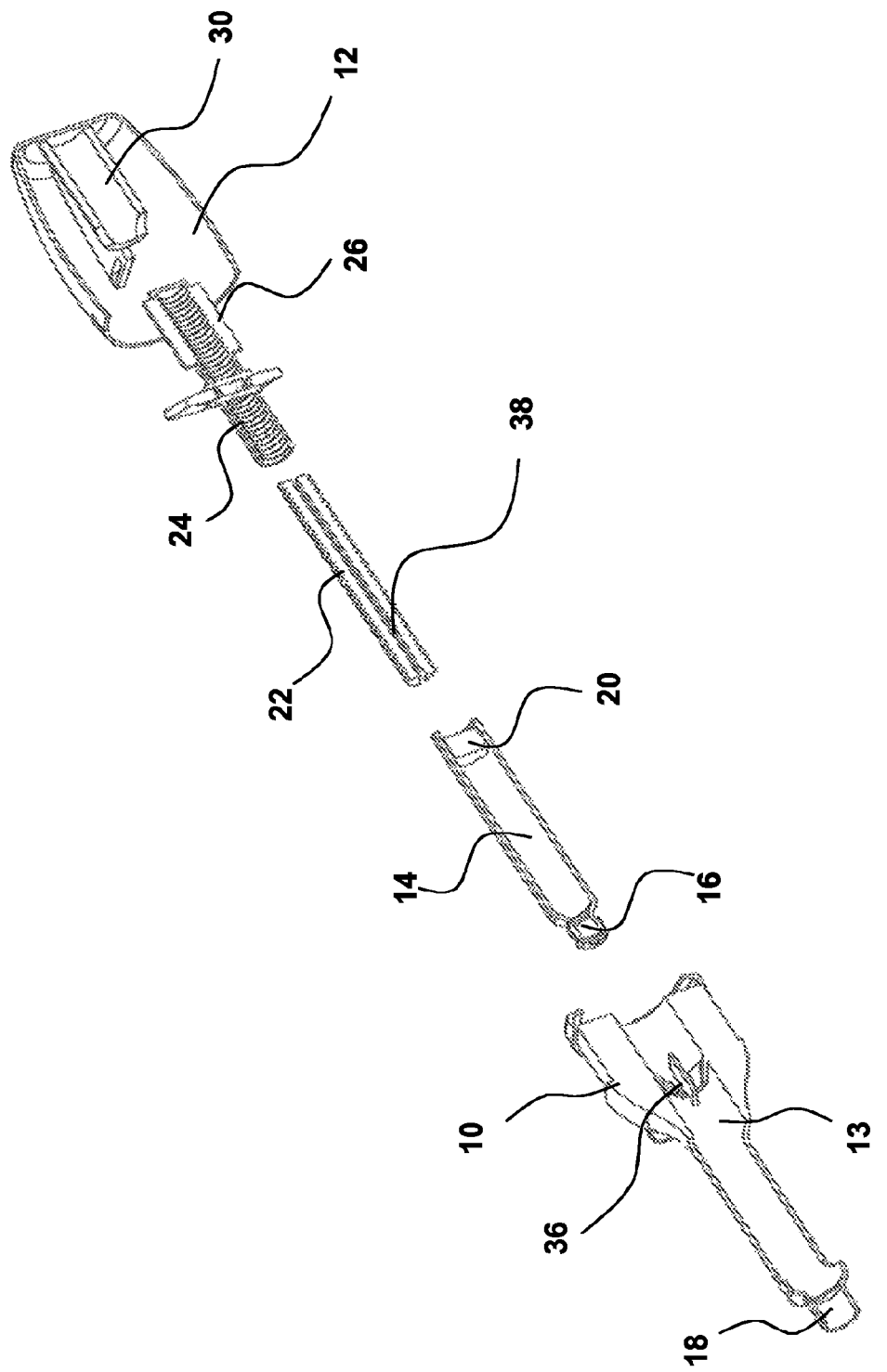
FIG. 4 is an exploded view of the device of FIG. 1.

The passage 13 of the proximal housing part 10 further comprises second locking members 36, such as longitudinally extending ledges, acting on corresponding second locking members 38, such as longitudinally extending grooves on said proximal plunger rod part 22; such that said second locking members 36 lock rotational movement of said proximal plunger rod part, FIG. 4.

The medicament delivery device further comprises a plate-shaped lever 46 pivotally attached to said proximal housing part 10, to said distal plunger rod part, and to said distal housing part 12.

Figure 2:
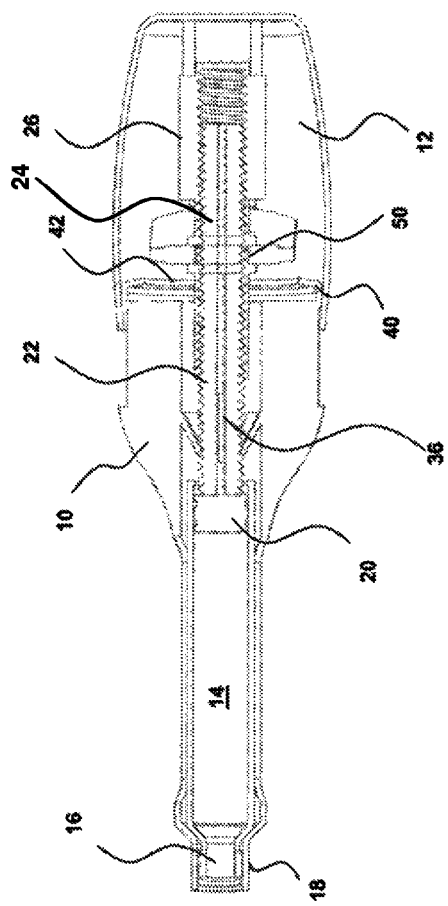
FIG. 2 is a cross-sectional side view of the device of FIG. 1.

The lever 46 comprises a central opening 48 through which the plunger rod 22, 24 extends, FIG. 3; first connecting means 50, such as shafts, arranged to pivotally interact with corresponding first connecting means 52, such as seats, of the distal plunger rod part, FIGS. 2 and 3; second connecting means, such as an elongated opening (not shown) arranged to pivotally interact with corresponding second connecting means 40, such as an annular ledge of the proximal housing part; and third connecting means 58, such as pin, arranged to pivotally interact with corresponding third connecting means 60, such as an elongated opening, of the distal housing part.

The device is intended to function as follows. When delivered to the patient or user, a medicament container 14 is preferably already placed inside the proximal housing part 10. When the user is to administer a dose of medicament a medicament delivery member is connected to the proximal neck portion 18 of the proximal housing part 10. A dose is then to be set. This is performed by turning the distal housing part 12 in relation to the proximal housing part 10. Because of the connection between the distal plunger rod part 24 and the distal housing part 12 due to the ledges 26 fitting into the grooves 28 of the tubular guide part 30, the distal plunger rod part 24 will also be turned. The proximal plunger rod part 22 is rotationally locked by the ledge 36 fitting into the longitudinal groove 38 of the proximal plunger rod part 22 and thus the distal housing part 12 will moved in the distal direction when the plunger rod parts are threaded in relation to each other for extending the plunger rod, which extension corresponds to a dose quantity to be delivered. The proximal plunger rod part 22 is further prevented from being moved in the distal direction by the inclined flexible arms 34 gripping the threads of the proximal plunger rod part. Because of the connection between the lever 46 and the distal plunger rod part 24 as well as the connection between the lever and the distal housing part 12, the lever 46 will also be turned, whereby the end of the lever connected to the annular ledge 40 is moved along its circumference at the distal end of the proximal housing part 10.

When a desired dose has been set, which may be indicated by indicia 62 on a side surface of the proximal housing part 10, FIG. 1, that becomes visible when the distal housing part 12 is moved in the distal direction during setting of a dose; a medicament delivery is to be performed. The user then grips the proximal housing part 10 preferably with two fingers pressing on protrusions or grip members 64, FIG. 1, while the palm of the hand or the thumb rests on the distal end wall 32 of the distal housing part 12, and the device is squeezed by the hand. This causes the distal housing part 12 to be longitudinally moved in the proximal direction in relation to the proximal housing part 10. This movement causes the end of the lever 46 connected to the distal housing part to be moved in the proximal direction. Because the other end of the lever is connected to the annular ledge 40 the lever 46 will pivot around that point. Because the lever 46 is also pivotally attached to the distal plunger rod part 24, the latter is also moved in the proximal direction. This further causes the proximal plunger rod part 22 to be moved in the proximal direction thereby acting on and displacing the stopper 20 inside the medicament container 14 whereby a dose of medicament is delivered through the medicament delivery member. Since the lever 46 is acting on the plunger rod, the force required to move the plunger rod during medicament delivery is greatly reduced.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
   a proximal housing part, the proximal housing part having at least two grip members configured for respective fingers of a user's hand;
   a distal housing part, the distal housing part having a distal end configured for a palm of the user's hand such that a portion of the proximal housing part extends in to the distal housing part;
   a medicament container arranged inside the proximal housing part;
   a plunger rod, comprising a proximal plunger rod part and a distal plunger rod part in threaded engagement with each other, wherein the proximal plunger rod part is movable in relation to the proximal housing part and in contact with a stopper of the medicament container, and the distal plunger rod part is connected to the distal housing part; and
   a lever pivotally attached to the proximal housing part, to the distal plunger rod part, and to the distal housing part;
   wherein the proximal and distal housing parts are operably interconnected to each other through the lever such that a relative rotation of the proximal and distal housing parts operates the lever for setting a dose and a clench of the user's hand pushes the proximal and distal housing parts together, such that the proximal housing part extends farther into the distal housing part, injecting the dose.

2. The medicament delivery device of claim 1, wherein the proximal housing part comprises first locking members that act on threads of the proximal plunger rod part such that the first locking members allow only proximal movement of the proximal plunger rod part.

3. The medicament delivery device of claim 2, wherein the proximal housing part comprises second locking members that act on corresponding second locking members of the proximal plunger rod part such that the second locking members block rotational movement of the proximal plunger rod part.

4. The medicament delivery device of claim 3, wherein the distal plunger rod part comprises an engagement device arranged to interact with a corresponding engagement device of the distal housing part for rotationally locking the distal plunger rod part and distal housing part in relation to each other, such that a rotation of the distal housing part in relation to the proximal housing part causes the distal plunger rod part to move a certain distance in a distal direction in relation to the proximal housing part and the proximal plunger rod and the lever to pivot, whereby the certain distance corresponds to a dose quantity to be delivered.

5. The medicament delivery device of claim 4, wherein the dose quantity is indicated by indicia on a side surface of the proximal housing part.

6. The medicament delivery device of claim 4, wherein relative longitudinal movement of the proximal and distal housing parts toward each other causes the distal housing part to act on the lever so as to proximally displace the proximal and distal plunger rod parts in relation to the proximal housing part to deliver the dose quantity.

* * * * *